United States Patent [19]

Shay et al.

[11] Patent Number: 5,177,003

[45] Date of Patent: Jan. 5, 1993

[54] **FLAVORED PROTEIN PRODUCTS DERIVED FROM *CANDIDA UTILIS***

[75] Inventors: Lucas K. Shay; Dennis S. Banasiak, both of Bartlesville; Trudy J. Fisher, Tulsa; Eugene H. Wegner, Bartlesville, all of Okla.

[73] Assignee: Phillips Petroleum Company, Bartlesville, Okla.

[21] Appl. No.: 615,541

[22] Filed: Nov. 19, 1990

Related U.S. Application Data

[63] Continuation of Ser. No. 39,553, Apr. 16, 1987, abandoned.

[51] Int. Cl.⁵ .................. C12P 21/04; C12N 1/16; C12N 1/20
[52] U.S. Cl. .................. 435/71.1; 135/255; 135/253.6; 135/804; 426/62
[58] Field of Search .............. 435/255, 253.6, 71.1, 435/804; 426/36, 62; 424/93

[56] References Cited

U.S. PATENT DOCUMENTS

| | | | |
|---|---|---|---|
| 3,865,691 | 2/1975 | Ridgway, Jr. et al. | 195/49 |
| 4,312,890 | 1/1982 | Liggett | 426/466 |
| 4,346,121 | 8/1982 | Turos | 426/580 |
| 4,466,986 | 8/1984 | Guggenbuehler et al. | 426/533 |
| 4,675,193 | 6/1987 | Boudreaux | 426/36 |

OTHER PUBLICATIONS

Chen et al., "Single-Cell Proteins in Food Applications", *Developments in Industrial Microbiology*, vol. 19, L. A. Undelkofler, ed. 1978 pp. 79-94.

Chang et al., "Romano cheese-like flavor developed by fungal lipase . . . " conference Abstract, J. Am. Oil. Chem Soc. (60,4,718)1983.

Boulx et al., *Biotech and Bioeng.*, vol 25, pp. 133-142, 1983.

Difeo Manual, 1977, 9th ed., pp. 269-270.

Kajs et al., Developments in Industrial Microbiology, vol. 21, 198, Chapt. 52, pp. 481-488.

*Primary Examiner*—Irene Marx
*Attorney, Agent, or Firm*—Lucas K. Shay

[57] ABSTRACT

A process is disclosed for improving the flavor of protein products derived from microorganisms which comprises heat treating the microorganism and then drying same in the absence of a centrifugation. Optionally, the microorganism can be cultured in the presence of a flavor enhancing additive.

4 Claims, No Drawings

FLAVORED PROTEIN PRODUCTS DERIVED FROM *CANDIDA UTILIS*

This application is a continuation of application Ser. No. 07/039,553, filed Apr. 16, 1987, now abandoned.

The present invention pertains to a process for enhancing the flavor of protein products which are derived from microorganisms. Another aspect of the invention pertains to protein products derived from microorganisms which have an enhanced flavor.

As a result of the current worldwide shortage of foods possessing a high protein content, there has been a great deal of research directed toward producing proteins from microorganisms. This research has led to the successful production of high quality protein products from microorganisms.

However, these protein products have not gained a widespread commercial acceptance. One of the primary reasons for this lack of commercial acceptance, is that these proteins often have a rather bland flavor that is unacceptable to most consumers.

Individuals have attempted to solve this problem, but none of their solutions have been entirely adequate.

For example, U.S. Pat. No. 4,312,890 broadly teaches that the flavor of yeast based food products can be improved by drying the fermentation broth and then roasting the dried yeasts. It also teaches that this process has had problems with charring of the yeast.

U.S. Pat. No. 4,466,986 teaches an alternative which avoids charring the yeast. It discloses lysing the yeast and running the resulting solution through a fractionation column. The amino acids collected in this process are then heated in the presence of a reducing sugar thereby conducting a Maillard reaction. This process has the disadvantage of requiring a separation step which decreases the yield of the final product.

It also suffers the disadvantage of requiring the presence of a reducing sugar in order to conduct the Maillard Reaction. Numerous fermentation media do not utilize a reducing sugar for their carbon source. Thus, if the carbon source is an alcohol, a paraffin, or sucrose, this process would not work without an additional step of adding a reducing sugar to the amino acids prior to the Maillard Reaction.

Therefore, it would be a valuable contribution to the art to develop a process that would enhance the flavor of protein products that are derived from microorganisms, without suffering from the disadvantages of the prior art.

It is an object of the present invention to provide a process that will enhance the flavor of protein products derived from microorganisms.

It is a further object of the present invention to provide protein products derived from microorganisms which possess an enhanced flavor.

In accordance with the present invention, it has been discovered that it is possible to enhance the flavor of protein products derived from microorganisms by heat treating the fermentation broth and then drying the broth in the absence of a centrifugation step.

In accordance with a further aspect of the present invention, it has been discovered that when microorganisms are cultured in the presence of a flavor enhancing additive suitable for consumption derived from an animal by-product or fatty acids and then heat treated and dried in the absence of a centrifugation step, there is obtained a further enhancement of the flavor of the protein products derived therefrom.

The process of the present invention can be utilized with microorganisms capable of producing nontoxic proteins. Suitable microorganisms include bacteria, yeasts, and molds. Yeasts are presently preferred.

Suitable yeasts include species from the genera Candida, Kluyveromyces, Hansenula, Torulopsis, Saccharomyces, Pichia, Debaryomyces, Lipomyces, Crytococcus, Nematospora, and Brettanomyces. The preferred genera include Candida, Kluyveromyces, Hansenula, Torulopsis, Pichia and Saccharomyces. Examples of suitable species of yeast include:

| | |
|---|---|
| Candida boidinii | Hansenula saturnus |
| Candida utilis | Hansenula californica |
| Candida stellatoidea | Hansenula mrakii |
| Candida robusta | Hansenula silvicola |
| Candida sake | Hansenula polymorpha |
| Candida claussenii | Hansenula wickerhamii |
| Candida rugosa | Hansenula capsulata |
| Brettanomyces petrophillum | Hansenula glucozyma |
| Hansenula minuta | Hansenula henricii |
| Hansenula nonfermentans | Pichia membranefaciens |
| Torulopsis candida | Pichia pinus |
| Torulopsis bombicola | Pichia pastoris |
| Torulopsis versatilis | Pichia trehalophila |
| Torulopsis glabrata | Saccharomyces cerevisiae |
| Torulopsis molishiana | Kluyveromyces fragilis |
| Torulopsis nemodendra | Saccharomyces rosei |
| Torulopsis nitratophila | Saccharomyces bailii |
| Pichia farinosa | Saccharomyces uvarum |
| Pichia polymorpha | Saccharomyces elegans |
| Kluyveromyces lactis | Saccharomyces rouxii |

Suitable bacteria include species from the genera Bacillus, Mycobacterium, Lactobacillus, Leuconostoc, Streptococcus, Pseudomonas, Methanomonas, Brevibacterium, Acetobacter, Corynebacterium, and Methylobacter. Preferred genera include Bacillus, Pseudomonas, Protaminobacter, Lactobacillus, Leuconostoc, Streptococcus, Arthrobacter and Corynebacterium.

| | |
|---|---|
| Bacillus subtilus | Pseudomonas fluorescens |
| Bacillus cereus | Pseudomonas oleovorans |
| Bacillus aureus | Pseudomonas putida |
| Bacillus circulans | Pseudomonas boreopolis |
| Bacillus magaterium | Pseudomonas pyocinia |
| Bacillus licheniformis | Pseudomonas methylphilus |
| Pseudomonas methanolica | Pseudomonas acidovorans |
| Protaminobacter ruber | Methylomonas methanolica |
| Mycobacterium rhodochrous | Leuconostoc bulgarions |
| Streptococcus cremoris | Lactobacillus bulgarions |
| Streptococcus lactis | Lactobacillus acidophilus |
| Streptococcus thermophilus | Leuconostoc citrovorum |
| Corynebacterium hydrocarbooxydans | Leuconostoc dextranicum |
| Mycobacterium phlei | Mycobacterium brevicale |
| Corynebacterium oleophilus | Corynebacterium glutamicum |
| Nacardia salmonicolor | Corynebacterium viscosus |
| Corynebacterium hydrocarboclastus | Corynebacterium dioxydans |
| Nocardia corallina | Corynebacterium alkanum |
| Nocardia butanica | Brevibacterium butanicum |
| Rhodopseudomonas capsulatus | Brevibacterium roseum |
| Microbacterium ammoniaphilum | Brevibacterium flavum |
| Arthrobacter parafficum | Brevibacterium lactofermentum |
| Arthrobacter simplex | Brevibacterium paraffinolyticum |
| Arthrobacter citreus | Brevibacterium ketoglutamicum |
| | Brevibacterium insectiphilium |
| | Methanomonas methanica |
| | Methanomonas methanooxidans |

Suitable molds include species from the genera Aspergillus, Monilia, Rhizopus, Penicillium, Mucor, Alternaria and Helminthosporium.

Examples of suitable species of molds include:

| | |
|---|---|
| Aspergillus niger | Penicillium griseofulvum |
| Aspergillus glaucus | Penicillium expansum |
| Aspergillus flavus | Penicillium digitatum |
| Aspergillus oryzae | Penicillium italicum |
| Aspergillus terreus | Rhizopus nigricans |
| Penicillium notatum | Rhizopus oryzae |
| Penicillium chrysogenum | Rhizopus delemar |
| Mucor mucedo | Rhizopus stolonifer |
| Mucor genevensis | Rhizopus arrhizus |

The most preferred microorganisms for use in the present invention include those yeasts which are currently approved by the FDA for human consumption. Examples of suitable species include *Candida utilis, Saccharomyces cerevisiae, Kluyveromyces fragilis,* and *Saccharomyces uvarum.*

Typically microorganisms are cultured by growing them on a suitable carbon energy source, under aerobic aqueous fermentation conditions employing an assimilable nitrogen source, mineral salts, molecular oxygen, with suitable pH and other controls, as are known in the art.

The particular fermentation method and apparatus used to culture the chosen microorganism is not critical to the practice of the present invention. There are numerous fermentation processes and apparatuses that are well known to those skilled in the art. Any of these well known fermentation processes and apparatuses are suitable for use with the present invention, provided it is appropriate for that particular microorganism.

For example, U.S. Pat. No. 4,617,274, Biochemical Conversions by Yeast Fermentation at High Cell Densities, issued to Eugene Wegner, which is currently assigned to Phillips Petroleum Company, teaches a suitable fermentation technique for use in the present invention.

The key to the practice of one embodiment of the invention is to introduce a flavor enhancing additive into the fermentation zone so that the chosen microorganism can be cultured in its presence.

There are currently two classes of flavor enhancers which are preferred for use in the present invention. The first class are those derived from animal by-products. The second class are fatty acids.

As used in this application, the term animal by-product refers to any composition derived from animal flesh which can be solubilized so that it can be introduced into the fermentation zone. Representative examples of suitable animal by-products for use in the present invention can be selected from the group consisting of beef extract, pork extract, turkey extract, or chicken extract. These products are available commercially from numerous suppliers.

The quantity of animal by-product which should be present in the fermentation zone is not critical to the practice of the present invention, but it is presently preferred that it be present in the range of from 0.5 to 5 weight/volume percent.

Suitable fatty acids for use in the present invention are those saturated fatty acids which contain from 4 to 10 carbon atoms. They can be represented by the following formula, RCOOH, wherein R is an alkyl group containing from 4 to 10 carbon atoms. The quantity of the fatty acid present in the fermentation zone is not critical to the practice of the present invention, but it is presently preferred that the fatty acids be present in the fermentation zone in the quantity of from 0.5 to 5 weight/volume percent.

At the present time, it is preferred to enzymatically generate an appropriate fatty acid in situ within the fermentation zone. This can be accomplished by adding a dairy product and the enzyme, lipase, to the fermentation zone.

Representative examples of suitable dairy products can be selected from the group consisting of butter, butter oil, cheese, milk, or cottage cheese. The quantity of dairy product introduced into the fermentation zone is not critical to the practice of the present invention, however, it is preferred that it be present in the quantity of from 0.5 to 5 weight/volume percent.

Likewise, it is not critical to the practice of the present invention, the quantity of the enzyme, lipase, which is present within the fermentation zone, but it is presently preferred that it be present in the range of 2,000 to 30,000 enzyme units per liter of ferment.

It is not critical to the practice of the present invention at what point during the fermentation process that the flavor enhancing additive is added to the fermentation zone. It is presently preferred, however, that it be introduced into the fermentation zone during the early phases of cell growth so that a more pronounced flavor can be developed.

The manner in which the flavor enhancing additive is added to the fermentation zone is not critical to the practice of the present invention. In continuous fermentation operations, the flavor enhancing additive can be added on a continuous basis along with the fermentation feed, whereas in batch fermentations it can be added at one time.

After the fermentation is completed in either embodiment of the invention, the fermentation broth is heat treated and dried in the absence of a centrifugation step, in order to enhance the flavor of the protein products produced therein. It is important to note that this improvement occurs whether or not a flavor enhancing additive is present during the fermentation process.

It is presently preferred to heat the fermentation broth to a temperature of 70°-99° C. for a period of time ranging from 2 to 20 minutes, or more preferably for 3 to 5 minutes at a temperature of from 80° to 85° C. The exact manner in which the fermentation broth is heated is not critical to the practice of the present invention. However, it is currently preferred to heat the broth within a heat exchanger.

After the heat treatment of the fermentation broth is completed, it is currently preferred that the fermentation broth be dried. The manner in which the fermentation broth is dried is not critical to the practice of the present invention provided that it does not encompass a centrifugation step. Spray drying or drum drying are representative examples of suitable methods. Spray drying is preferred.

If it is desirable in a particular fermentation process, the fermentation broth can be concentrated prior to the heat treatment by vacuum concentration/condensation or any other technique conventionally used which does not entail a centrifugation step that would remove soluble ingredients.

Examples are provided to assist in a further understanding of the invention. Particular materials employed, species, and conditions are intended to be further illustrative of the invention and not a limitation thereof.

EXAMPLE I

The purpose of this example is to demonstrate that the flavor of the protein products produced in accordance with the prior art is unappealing to most consumers.

In a continuous aerobic fermentation process, aqueous mineral salts medium and sucrose were fed to a fermenter inoculated with the yeast species *Candida utilis* NRRL Y-1082, at a rate such that sucrose was the growth-limiting nutrient. The fermentor was a 1500-liter foam-filled fermentor with a liquid volume of about 610 liters, with automatic pH, temperature, and level control. Agitation was provided by two conventional paddle-type turbines driven at 800 rpm. The aeration rate was about 4 volumes of air, at about 38 psig and about 25° C. per volume of ferment in the fermentor per minute. Anhydrous ammonia was added at a rate sufficient to maintain a pH of about 4 in the fermentation mixture.

The aqueous fermentation medium was prepared by mixing, with each liter of tap water, 11.9 mL of 75 weight percent $H_3PO_4$, 6.4 gm of $K_2SO_4$, 5 gm of $MgSO_4.7H_2O$, 0.3 gm of $CaSO_4.2H_2O$, 1.8 gm of 85 weight percent KOH, and 275 gm of sucrose. The aqueous fermentation medium was fed into the fermenter at a rate of 100 to 110 liters per hour.

The trace mineral solution was prepared by mixing for each liter of solution 60 gm of $FeSO_4.7H_2O$, 1.5 gm of $Na_2MoO_4.2H_2O$, 0.2 gm of $CoCl_2.6H_2O$, 38 gm of $ZnSO_4.7H_2O$, 2.5 gm of $MnSO_4.H_2O$, 5 gm of $CuSO_4.5H_2O$ and 4 mL of concentrated $H_2SO_4$ and sufficient deionized water to make 1 liter of solution. The trace mineral solution was fed into the fermenter at a rate of 400 to 444 mL per hour.

The fermentation was conducted at about 34° C. and about 38 psig pressure, with an average retention time of about 5 to 6 hours. The cell density was typically about 140 grams of cells per liter of fermenter broth. The total solid contents of the fermenter was typically about 150 grams per liter.

The resulting yeast cells wer separated from the fermentation broth by centrifugation, washed by suspension in water, followed by recentrifugation, dried via a spray drier and weighed. On a dried basis the yield of yeast cells typically was about 50 to 54 gm per 100 gm of sucrose.

Yeast produced in this manner had a very bland flavor that was found unappealing by the taste tester. They had an off-white color.

EXAMPLE II

The purpose of this example is to demonstrate that when the fermentation broth is heat treated and dried in the absence of a centrifugation step, there is obtained a protein product of improved taste.

An inoculumn of *Candida utilis* NRRL Y-1082 was fermented in the manner described in Example I.

Instead of recovering the cells in the manner of Example I, the following procedure was followed.

The fermentation broth was pumped through a heat exchanger having a temperature of 80° to 85° C. at the rate of 25 gallons per hour. This meant that the fermentation broth was heat treated for a period of time ranging from 3 to 5 minutes.

After the fermentation broth had been heat treated, it was then dried via a spray drier. The resulting powdered yeast had a light tan color and a much improved flavor.

EXAMPLE III

The purpose of this example is to demonstrate that when a microorganism is cultured in the presence of a flavor enhancing additive, there is obtained a protein product of improved taste.

An inoculum of *Candida utilis* NRRL Y-1082 was fermented in the manner described in Example I, except that it was fermented in the presence of beef extract.

This was accomplished in the following manner. The inoculum was cultured on an aqueous fermentation medium identical to that of Example I until the ferment had reached a total weight of 350 kg. At that point, a new aqueous fermentation medium was fed to the fermentation zone at the rate that the contained sucrose could be consumed instantly. The new fermentation medium was identical to the aqueous fermentation medium of Example I, except that it contained 33 gm of beef extract per liter of fermentation medium.

The inoculum was cultured until the ferment had reached a total weight of 800 kg. At that point the fermentation was stopped and the fermentation broth was heat treated in the following manner.

The fermentation broth was pumped through a heat exchanger having a temperature of 82° C. at the rate of 25 gallons per hour. This meant that the fermentation broth was heat treated for a period of time ranging from 3 to 5 minutes.

After the fermentation broth had been heat treated, it was then dried via a spray dryer. The resulting powdered yeast had a flavor characteristic of beef and had an appealing light tan color.

EXAMPLE IV

The purpose of this example is to demonstrate that culturing a microorganism in the presence of fatty acids will improve the flavor of the protein products derived therefrom.

In a continuous aerobic fermentation process, sucrose and an aqueous mineral salts medium were fed to a fermenter inoculated with the yeast species *Candida utilis* NRRL Y-1082 at a rate such that sucrose was the growth-limiting nutrient. The fermentor was a two-liter foam-filled fermenter with a liquid volume of about 1800 mL, with automatic pH, temperature, and level control. Agitation was provided by two conventional paddle-type turbines driven at 1000 rpm. The aeration rate was 4 volumes of air at about 25° C. per volume of of ferment in the fermenter per minute. Anhydrous ammonia was added at a rate sufficient to maintain a pH of about 4 in the fermentation mixture.

The aqueous mineral salts in sucrose medium was prepared by mixing, with each liter of tap water, 11.9 mL of 75 weight percent $H_3PO_4$, 6.4 gm of $K_2SO_4$, 7.8 gm of $MgSO_4.7H_2O$, 0.3 gm of $CaSO_4.2H_2O$, 1.8 gm of 85 weight percent KOH, 275 gm of sucrose and 0.8 gm of lipase. The aqueous mineral salts and sucrose medium was fed at a rate of 130 to 146 mL per hour.

The trace mineral solution was prepared by mixing for each liter of solution 60 gm. of $FeSO_4.7H_2O$, 38 gm. of $ZnSO_4.7H_2O$, 2.5 gm. of $MnSO_4.H_2O$, 5 gm. $CuSO_4.5H_2O$, 1.5 gm of $Na_2MoO_4.2H_2C$, 0.2 gm $CoCl_2.6H_2O$, 4 mL of concentrated $H_2SO_4$ and sufficient deionized water to make 1 liter of solution. 4.0 to 4.5 mL of this trace mineral solution was added to each liter of the above-described aqueous mineral and sucrose solution.

The fermentation was conducted at about 34° C. with an average retention time of about 5 to 6 hours. The cell density typically was about 140 gm. of cells per liter of fermenter broth. The total solid contents of the ferment typically was about 150 gm. per liter.

In addition to the above-described aqueous mineral and sucrose feed, butter oil was also added to the fermentation zone at the rate of 0.11 mL per minute.

The fermentation was then conducted for 20 hours. After 20 hours, a 500 mL sample was withdrawn.

The rate at which the butter oil was pumped into the fermentation zone was then increased to 0.22 mL per minute and the fermentation was conducted for another 20 hours. At the end of that 20 hour period, another 500 mL sample was withdrawn.

Both of the 500 mL samples were heat treated with a hot plate at 80° C. for 3 to 5 minutes. They were then spray-dried.

The resulting powders tasted like blue cheese. They also had an aroma reminiscent of bleu cheese. They were light tan in color.

Thus, this example demonstrates that when a microorganism is fermented in the presence of fatty acids, there is a dramatic improvement in the taste of the resulting proteins derived therefrom.

That which is claimed is:

1. A process for the production of an enhanced flavored yeast which comprises:
    a) culturing *Candida utilis* NRRL Y-1082 in a fermentor in the presence of a soluble flavor enhancing additive suitable for human consumption which is selected from the group consisting of beef extract, pork extract, and turkey extract;
    b) heating the resulting fermentation broth at 70° C. to 99° C. for about 2 to about 20 minutes; and thereafter
    c) drying the resulting heat-treated fermentation broth; wherein said flavor enhancing additive is present in the fermentation broth at the beginning of fermentation in the quantity of from 0.5 to 5 weight/volume percent.

2. A process according to claim 1 wherein said flavor enhancing additive is beef extract, said fermentation broth is heated to a temperature of 80° C. to 85° C. for 3 to 5 minutes, and said heat-treated fermentation broth is spray dried.

3. A process for the production of enhanced flavored protein product in yeast which comprises:
    a) culturing *Candida utilis* NRRL Y-1082 in a fermentor in the presence of short chain saturated fatty acids having 4 to 10 carbon atoms which are generated in-situ within the fermentor by introducing butter and a lipase into said fermentor;
    b) heating the resulting fermentation broth at 70° C. to 99° C. for about 2 to about 20 minutes; and thereafter
    c) drying the resulting heat-treated fermentation broth; wherein said butter is present in the fermentation broth in the quantity of from 0.5 to 5 weight/volume percent and said lipase is present in the quantity of 2,000 to 30,000 enzyme units per liter fermentation broth.

4. A process according to claim 3 wherein said fermentation broth is heated to a temperature of 80° C. to 85° C. for 3 to 5 minutes and said heat-treated fermentation broth is spray dried.

* * * * *